United States Patent
Anzellini et al.

(12) 
(10) Patent No.: US 6,339,720 B1
(45) Date of Patent: Jan. 15, 2002

(54) EARLY WARNING APPARATUS FOR ACUTE MYOCARDIAL INFARCTION IN THE FIRST SIX HOURS OF PAIN

(76) Inventors: Fernando Anzellini, Calle 83 No. 19-36 (of. 704), Bogota; Arturo Sesana, Calle 100 No. 35-67 Ap 616, Sta Fe de Bogota; Mario Gongora, Carrera 13 No. 90-55 Ap. 404, Sta Fe de Bogota, all of (CO)

( * ) Notice: Subject to any disclaimer, the term of this patent is extended or adjusted under 35 U.S.C. 154(b) by 0 days.

(21) Appl. No.: 09/399,320

(22) Filed: Sep. 20, 1999

(51) Int. Cl.$^7$ .......................................... A61B 5/0452
(52) U.S. Cl. ..................................................... 600/517
(58) Field of Search ............................. 600/517, 516, 600/519, 509

(56) References Cited

U.S. PATENT DOCUMENTS

| | | |
|---|---|---|
| 2,315,064 A | 3/1973 | Buchard |
| 3,868,567 A | 2/1975 | Ekstrom .................... 324/77 A |
| 3,991,747 A | 11/1976 | Stanly ......................... 600/510 |
| 4,006,737 A | 2/1977 | Cherry ....................... 128/702 |
| 4,073,011 A | 2/1978 | Cherry ....................... 128/711 |
| 4,299,233 A | 11/1981 | Lemelson ................... 128/687 |
| 4,318,412 A | 3/1982 | Stanly et al. ............... 600/508 |
| 4,362,164 A | 12/1982 | Little ......................... 128/639 |
| 4,546,776 A | 10/1985 | Bellin et al. ................ 128/704 |
| 4,628,939 A | 12/1986 | Little ......................... 128/696 |
| 4,679,144 A | 7/1987 | Cox et al. .................... 600/516 |
| 4,838,275 A | 6/1989 | Lee ............................. 128/670 |
| 4,930,075 A | 5/1990 | Kortas ................... 364/413.06 |
| 4,957,115 A | 9/1990 | Selker ......................... 600/509 |
| 5,003,983 A | 4/1991 | Dingwall, et al. .......... 128/704 |
| 5,042,497 A | 8/1991 | Shapland .................... 128/696 |
| 5,058,597 A | 10/1991 | Onoda et al. ................ 600/509 |
| 5,135,004 A | 8/1992 | Adame ........................ 128/696 |
| 5,181,519 A | 1/1993 | Bible .......................... 600/517 |
| 5,226,424 A | 7/1993 | Bible .......................... 600/508 |
| 5,235,976 A | 8/1993 | Spinell .......................... 607/25 |
| 5,433,209 A | 7/1995 | Gallant ....................... 128/711 |
| 5,456,261 A | 10/1995 | Luczyk ....................... 600/515 |

(List continued on next page.)

FOREIGN PATENT DOCUMENTS

| | | |
|---|---|---|
| DD | 281 957 A5 | 8/1990 |
| DE | 2315064 | 3/1973 |
| DE | 3633-983 A | 10/1986 |
| GB | 2 061 521 A | 5/1981 |
| JP | 5-64632 A | 3/1993 |
| JP | 405176906 A | 7/1993 |
| SU | 1570-709 A | 6/1990 |

*Primary Examiner*—Scott M. Getzow

(57) ABSTRACT

A portable device (8) for recognizing Acute Myocardial Infarction by the patient himself without the help of medical doctors or technicians is described. The invention performs a real-time analysis of the ST segment (9) in an ambulatory electrocardiographic measurement environment to help the patient decide by himself that he is suffering an Acute Myocardial Infarct. The device (8) is capable of warning the user that he/she may be suffering a heart attack when the ST segment (9) is found to be depressed or elevated. The CARDIOST features a simple-to-use portable electrocardiographic amplifier (15) and a microcontroller unit (17) to analyze the ST segment (9) on the signal received from the electrocardiographic amplifier (15). With a software embedded in the microcontoller unit (17) the analysis of the ST segment (9) delivers the diagnosis to the patient with a visual and acoustic alarm (18,19,20,21) representing low, medium or high risk, depending on the status of the ST segment (9) shift so that he can seek medical treatment for thrombolisys or any other treatment currently available and influenced by early diagnosis within 4–6 hours without misinterpreting subjective chest pain symptoms, this being a worldwide medical problem since Acute Myocardial Infarction is the leading cause of mortality in the world.

2 Claims, 8 Drawing Sheets

U.S. PATENT DOCUMENTS

| | | | |
|---|---|---|---|
| 5,462,504 A | 10/1995 | Trulaske | 482/7 |
| 5,464,020 A | 11/1995 | Lerner | 600/508 |
| 5,562,711 A | 10/1996 | Yerteh | 607/17 |
| 5,584,868 A | 12/1996 | Salo | 607/17 |
| 5,662,688 A | 9/1997 | Haefner | 607/5 |
| 5,683,444 A | 11/1997 | Huntiey | 607/122 |
| 5,685,303 A | 11/1997 | Rollma | 128/644 |
| 5,713,367 A | 2/1998 | Arnold | 128/704 |
| 5,718,233 A | 2/1998 | Selker et al. | 128/696 |
| 5,792,066 A | 8/1998 | Kwong | 600/517 |
| 5,813,979 A | 9/1998 | Wolfer | 600/373 |
| 5,876,351 A | 3/1999 | Rohde | 600/523 |

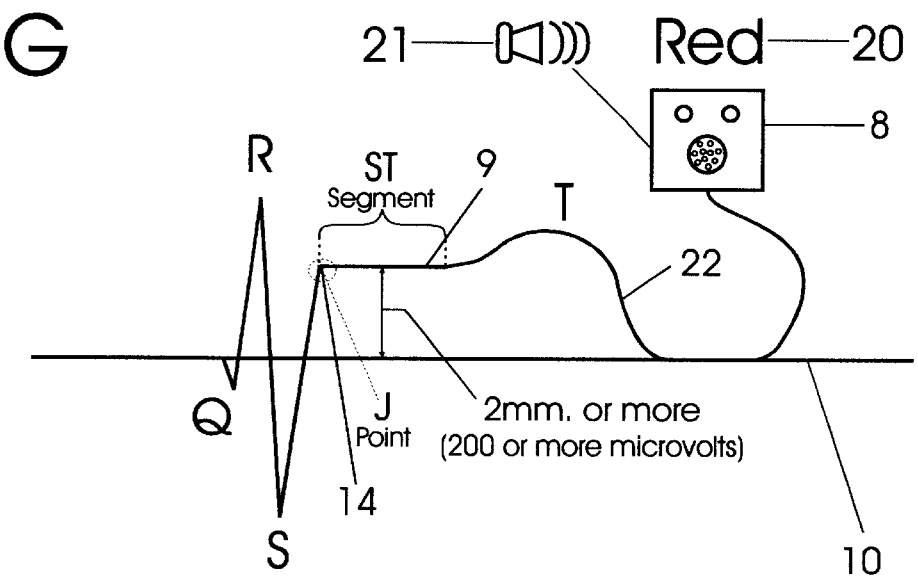

PROGRAM FLOW DIAGRAM

EARLY WARNING APPARATUS FOR ACUTE MYOCARDIAL INFARCTION IN THE FIRST SIX HOURS OF PAIN

CROSS REFERENCE TO RELATED APPLICATIONS

Not applicable

BACKGROUND

1. Field of Invention

The CARDIOST relates to a unit capable of informing a user with no medical background when he/she is suffering an Acute Myocardial Infarction in the first 4 to 6 hours of chest pain.

2. Description of Prior Art

There are many electrocardiographic (ECG) measuring apparatuses. Many of them can measure the ST segment (and other parts of the electrocardiogram wave) but are not meant to alert as to the possibility of an Acute Myocardial Infarction, and they have to be used by qualified medical personnel.

The portable electrocardiographic monitoring devices are used for long-term collection of ST segment data and many other measurements. Some of these devices perform simple real-time analyses limited to ischemia period detection and recording. These devices are used over a long period of time (usually 24 hour periods) for passive recording and analysis. After this period the data has to be downloaded from the device and analyzed by qualified medical personnel for the final opinion. These devices have to be carried by the patient for the complete period of data recording, which makes them uncomfortable no matter how small they are.

U.S. Pat. No. 5,433,209 issued to Gallant et al. July 1995 fully describes an ambulatory recording device that measures the ST segment for further analysis by a physician, which is incorporated herein as reference entitled "recorder unit for ambulatory ECG monitoring system". This unit does not measure the ST segment in immediate analysis and therefore is not able to diagnose Acute Myocardial Infarction in real time at the moment of real pain when it is necessary for the patient to seek medical advice for early thrombolysis. This Patent is intended to analyze all the waves of the electrocardiogram other than the ST segment and the baseline. The mentioned Patent also includes accumulation and recording of "minute-by-minute", "hour-by hour" and "end of period" summary information that is not used in acute settings.

U.S. Pat. No. 5,713,367 issued to Arnold et al. February 1998 for measuring and assessing cardiac electrical stability and the alternans pattern of cycle-to cycle variability in physiologic waveforms does not measure S-T segment but alternans of the QRS wave to asses the risk of ventricular arrythmias, as does the signal average electrocardiogram by averaging many repetitive waveforms, and much of the existing hardware can be used for both systems. Neither of these systems is intended for acute ischemia diagnosis.

U.S. Pat. No. 5,584,868 issued to Salo et al. December 1996 is a cardiac stimulating apparatus and method for heart failure therapy that includes a dual chamber pacemaker on an invasive basis that is not intended with our invention, and a cardiac defibrillator for reducing cardiac lethal arrythmia and sudden death by the means of electric shock provided by the defibrillator.

U.S. Pat. No. 3,868,567 issued to Ekstrom et al. February 1975 is related to the PQ level of the same waveform employing delta modulation and demodulation for processing information overlapping the ST segment with a predetermined electrocardiographic form and making an average between two segments of waveforms, but does not trigger any visual or audible alarm intended for early diagnosis of Acute Myocardial Infarction.

U.S. Pat. No. 3,991,747 issued to Stanly et al. November 1976 is a electrocardiographic device for telephonic or radio transmission to an analyzing facility, converting the signs to audio output, not intended to be analyzed by the patient himself, and displays the full extent of the 12 EKG leads. The device described in this Patent does not have an audio or visual alarm.

U.S. Pat. No. 4,318,412 issued to Stanly et al. March 1982 is intended to provide and optimize the placement of cardiac electrodes and to improve the signal processing but is not intended for early diagnosis of Acute Myocardial Infarction nor does it examine the ST segment. This arrangement obtains 90% of the information from a 12-lead electrocardiogram.

U.S. Pat. No. 4,546,776 issued to Bellin et al. October 1985, which analyzes PQ and ST portions of an electrocardiogram waveform and establishes a normal or standard ST ratio deviation between the difference of ST and PQ level, has an actuating alarm if heartbeats exceeds or is lower than a predetermined rate. When the ST segment triggers the alarm it is made on the basis of a standard ST deviation value in this Patent. Also it is emphasized that the ST segment is measured continuously. This invention is intended to be used in exercise conditions such as jogging. While this Patent indicates that a depression of approximately 100 microvolts is usually "normal", we consider that this degree of depression in acute pain is enough to trigger an alarm of "medium risk" (yellow light). In this Patent the alarm is intended in part to warn the user to "cease vigorous activity" and does not seek an immediate use of thrombolisys. The PQ level is used and compared to the ST level instead of comparing to the baseline, which is universal in the electronic signal of any electrocardiogram.

U.S. Pat. No. 4,679,144 issued to Cox et al July 1987 includes a programmable apparatus carried by an ambulatory patient for performing continuous real time analysis of EKG information by permanently carrying the device and analyzing the TP segment against the ST segment. Emphasis is made on the slope of the current EKG amplitude minus previous EKG amplitude, so only the patient intended to use the apparatus can take advantage of the diagnosis instead of any other person where the baseline is used as reference.

U.S. Pat. No. 4,930,075 issued to Kortas et al. May 1990 focuses only on the quantification of the ST depression, slope and length of the ST segment and is a software implemented method for analysis, but is not intended as a device for self diagnosis of acute ischemia. It studies principally a precise mathematical relationship between the values of the S-T segment.

U.S. Pat. No. 4,957,115 issued to Selker et al. September 1990 is intended as a device for determining the probability of death in cardiovascular patients and a method for assessing mortality risk at a health care facility. It is a computer adapted to receive the output and calculate a numerical value representing the output-based probability.

U.S. Pat. No. 5,003,983 issued to Dingwall et al. April 1991 is intended to provide an improved cardiac monitoring system to measure the deviation of the S-T segment and pulse rate in a package that can be easily and unobtrusively attached to a patient, for example, during an exercise routine, or long term monitoring.

U.S. Pat. No. 5,058,597 by Onoda et al. October 1991 has an R wave detector determining the heart rate and the ST value of the ECG signal over a long period of time while being carried by a subject who presses an event switch on feeling a subjective symptom (includes pain) but, instead of triggering an alarm after analyzing the ST segment, the electrocardiographic signal is written to another storage which is assigned to waveforms. The electrocardiograph records a minimum necessary amount of information for screening, i.e. the heart rates, ST values, and waveforms of electrocardiographic signal associated with subjective symptoms.

U.S. Pat. No. 5,181,519 issued to Bible et al. January 1993 detects the ST segment but is not intended to trigger an alarm when any shift of the segment is detected, the associated signal is then stored while the monitoring unit continues to search for further measured ST deviations exceeding the threshold ST deviation and subsequently the recorded signals and associated data can be displayed by transmitting it from the monitoring unit to a remote display unit via a data transmission unit.

U.S. Pat. No. 5,226,424 issued to Bible et al. July 1993 determines the ST segment characteristics useful in diagnosing myocardial ischemia, but operates continuously and focuses on a low energy consumptive portable heart monitor which derives from the fact that processing of the analog data requires considerably less energy than does processing the digital data continuously in normal operating mode and is not intended to trigger an alarm when Acute Myocardial Infarction occurs.

U.S. Pat. No. 5,456,261 issued to Lucky et al. October 1995 analyzes a plurality of the electrocardiographic signals for determining the existence of rhythm abnormalities, infarction, hypertrophy and repolarization abnormalities, and is not a solution for early and immediate diagnosis of acute ischemia and infarction self made by the patient himself.

U.S. Pat. No. 5,464,020 issued to Lerner et al. November 1995 is intended for the diagnosis of subacute cardiac dysfunction and not for acute ischemia.

U.S. Pat. No. 5,718,233 issued to Selker et al. February 1998 is only for continuous monitoring in a patient who has a cardiovascular disease and is a predictive instrument for computing a patient's probability of a serious cardiac condition, it is not intended to be used in acute settings and pain.

U.S. Pat. No. 5,792,066 issued to Kwong et al. August 1998 is intended to be used in patients who have underlying heart conditions which mimic Acute Myocardial Infarction, and remedies a deficiency in the prior art methods and systems for this diagnosis by detecting a wave amplitude ratio (e.g. the ST complex amplitude divided by the S wave component amplitude at some specified instant in time). It calculates and compares to predetermined criteria and on the basis of this comparison it indicates whether Acute Myocardial Infarction is occurring. Thus it is unique in diagnosis only for the patient who uses the device but cannot be used by any other person if pain is present because it compares ST amplitude divided by S wave component of the same patient against a predetermined criteria rather than against the baseline which is universal for any electrocardiogram, and does not provide any audible or visual alarm triggered by the ST segment shift.

U.S. Pat. No. 5,813,979 issued to Wolfer et al. September 1998 describes storable conductors for expeditiously facilitating the manual administration, storage and dispensing of individual electrode leads to a patient in emergency situations when setup and operation is difficult, and is not intended for self-diagnosis of Acute Myocardial Infarction by the patient in acute pain.

U.S. Pat. No. 5,876,351 issued to Rohde et al. March 1999, in which a medical component is removable and connected to the platform has specialized circuitry specific to a predetermined medical function. It is used for obtaining ECG in a cost-effectiveness basis designed primarily for playing video games.

U.S. Pat. No. 5,562,711 issued to Yerich et. al. October 1996 is provided with circuitry for sensing a plurality of physiologic parameters intended to be indicative of increased cardiac output and is a body implantable cardiac pacemaker.

U.S. Pat. No. 5,662,688 issued to Haefner et al. September 1997 is a system and method that automatically controls a gain of a cardioverter/defibrillator and delivers shock pulses in response thereto. A detection circuit detects depolarizations and provides a signal representing a cardiac event indicative only on depolarization.

U.S. Pat. No. 5,683,444 issued to Huntley et al. November 1977 is an implantable assembly for defibrillation in the form of flexible electrode that delivers energy more efficiently to body tissues than conventional defibrillation electrodes.

U.S. Pat. No. 5,462,504 issued to Trulaske et al. October 1995 is a method and apparatus for maintaining the heart rate of a user of a fitness apparatus and is intended to be incorporated into a treadmill.

U.S. Pat. No. 4,073,011 issued to Cherry et al. February 1978 is an electrocardiographic computer with a multi-speed magnetic tape scanning device for processing and observing in a relatively short interval of time large quantities of ECG signals from two pairs of ECG leads.

U.S. Pat. No. 4,006,737 issued to Cherry February 1977 is a device for processing and observing in a relatively short interval of time large quantities of ECG signals from two pair of ECG leads. The trend information is heart rate and ST segment level to provide a scanning of an entire 24 hour tape in 12 minutes.

U.S. Pat. No. 4,299,233 issued to Lamelson November 1981 is a device on which a human body may lie or recline for body vibrations such as heart pulses, respiration or body tremors. A transducer is operatively coupled to the liquid.

U.S. Pat. No. 4,362,164 issued to Little et al. December 1982 is a audio transducer that has a body which on one side mounts an electrode carrying chest belt. A microphone and a rotor assembly are mounted in a cavity in the body, and communicates through passages in the rotor assembly with the electrode carrying chest bell when the rotor assembly is in a first position and with the conventional chest bell when the rotor assembly is rotated to a second position.

U.S. Pat. No. 4,628,939 issued to Little et al. December 1986 is a method and associated means for producing simultaneous electrical representations of the electrical and acoustic activity of the heart in which a pickup device and associated circuits produce a full wave rectified symmetrical heart sound signal annotated by pulses developed from the QRS wave of the electrocardiogram signal.

U.S. Pat. No. 4,838,275 issued to Lee June 1989 is an apparatus that includes special furniture on which the patent lies an sits, and embedded in which are devices that automatically sense multiple parameters related to the patient's health. The patient cooperates only passively and transmits these signals from the patient's home to a central surveillance and control office.

U.S. Pat. No. 5,042,497 issued to Shapland August 1991 is a system for predicting and preventing cardiac arrhythmia for the use in combination with an implanted arrhythmia treatment device. The preventative actions include overdrive pacing of the heart.

U.S. Pat. No. 5,135,004 issued to Adams et al. August 1992 is an implantable device that assists in the diagnosis of myocardial ischemia of a human heart and includes a plurality of electrodes and a like plurality of sense amplifiers for generating an electrogram for each of the electrodes. A digital to analog converter reads the voltage magnitudes of the electrocardiogram ST segments which are then stored in a memory. An implantable receiver,transmitter is arranged to transmit the magnitudes of the electrocardiogram ST segments to a nonimplanted external receiver.

U.S. Pat. No. 5,181,519 issued to Bible January 1993 is a portable apparatus and method for monitoring heart muscle electrical activity includes a plurality of electrical contacts that transmits the signals to the monitoring unit. Whenever a series of ST segments exhibit an ST deviation from the reference axis which exceeds a predetermined threshold deviation, the monitoring unit records data relating thereto which is used for diagnosis of myocardial ischemia.

U.S. Pat. No. 5,235,976 issued to Spinelli August 1993 is a cardiac rhythm management device in which the rate controlling parameter of a rate adaptive pacemaker is the heart's total active time used as an indication of hemodinamic instability for triggering a defibrillation.

U.S. Pat. No. 5,685,303 issue to Rollman et al. November 1977 is a belt like strip for recording electrocardiograms insuring proper placement on the patient's chest or precordium during usage.

Foreigns Patents No GB 2061521A issued to DavisHowell Jenkins May 1981 measures the individual's susceptibility to cardiovascular disorder with a visual indicator displaying one of a series of indications and enabling answers to be entered. Patent SU 1570-709-A issued to Leca June 1990 is a human's heart action monitor that measures heart contraction frequency and ST segment shift. U.S. Pat. No. 2,315,064 issued to Burchard March 1973 measures ST fall arrhythmia's with continuously selectable prematurity index and intervals, tachy- and bradycardias, in continuously adjustable intervals and/or frequency regions. Patent DD 281 957 A5 issued to Krinke August 1990 determines the time occurrence of R-blips, QRS complexes and P-waves and allows a complex description of irregularity as well as formulation. Patent DE 3633-983 A issued to Wasser October 1986 measures variations in voltage characteristics and provides a high degree of freedom movement, different output signals are provided in dependence on the variation rate. Patent 5-64632 (A) issued to Takashi Suzuki March 1993 enables quick finding of calculating conditions ensuring a better ST deviation trend graph. Patent 405176906 (A) issued to Mutsuo Kaneko July 1993 measures a peak value of ST segment at an arbitrary measuring point displaying successively generated ST trend graphs, so that many derived electrocardiogram waveforms can be recognized easily.

SUMMARY

The object of the CARDIOST is to provide a device capable of instantaneous electrocardiographic measurement and real-time analysis of the ST segment in order to detect an Acute Myocardial Infarction so that a user can differentiate it from other types of chest pain through code color-audible alarms and seek immediate medical attention before 4–6 hours for proper treatment to be installed. This device can be used by the owner himself or by any other nearby person because it uses as reference for the ST segment shift the baseline of the electrocardiogram which is universal for everyone.

OBJECTS AND AN ADVANTAGES

Accordingly, the main objects and advantages of our CARDIOST are that it allows for a real-time diagnosis made by the patient himself at the time of acute pain and thus enables him/her to seek immediate medical attention for precordial pain. Failure to consult immediately is one of the leading causes of mortality and morbidity in Acute Myocardial Infarction (AMI) which in itself is a leading cause of mortality in humans. Not to consult within 4–6 hours of acute pain is one of the major public health problems in the world, as supported by thousands of papers and studies all over the world. Other devices which make automatic diagnoses of Acute Myocardial Infarction need to be read and interpreted by a physician who most of the time is not available when the patient really needs the diagnosis.

Another object of the CARDIOST is to provide a portable apparatus, small in size, of light weight, and with a low power consumption, which can measure electrocardiographic data and analyze same digitally and instantaneously.

It is a further object of our CARDIOST to provide a device that measures either a positive or negative ST segment shift from the baseline, providing the user within seconds of the measurement with a warning of a possible Acute Myocardial Infarction.

It is yet another object of CARDIOST to provide a device capable of instantaneous electrocardiographic measurement that can be used easily by any person, preferably the patient himself, even if such person is under the stress of thinking that he/she is having a heart attack.

Finally, the CARDIOST is designed to help a patient to distinguish between the common symptoms of chest pain and those of Acute Myocardial Infarction, which is usually very confusing and subjective.

These and other purposes of the CARDIOST are achieved by means of the embodiment of a portable electrocardiographic measuring and analyzing unit, preferably a small, low-power electronic unit. The electronic unit consists of an electrocardiographic signal amplifier connected to the patient via a five-lead electric connection, a positive electrode at the rear of the device, and a neutral electrode also at the rear part of the device, both of which make contact with the precordial skin of the patient, and three more electrodes placed in the left armpit, right armpit and lower abdominal wall (hipogastrium). The device then immediately measures the signal.

The signal from the electrocardiographic amplifier is digitized by an ADC (Analog to Digital Converter) unit and recorded for a few seconds by an electronic analysis unit consisting preferably of an electronic microcontroller.

The electronic analysis unit extracts the ST segments of the electrocardiographic signal and measures its elevation or depression in relation to the baseline. The ST segment of a typical healthy heart is a straight line of zero slope on or near a horizontal reference axis; if there is a significant deviation from the reference axis, the heart muscle signal is termed anomalous which is indicative of an unhealthy heart muscle. It is of primary importance for the electrocardiogram not to be analyzed against a predetermined and stored reference or normal value for the patient but against the baseline so it can be used not only by the owner himself of the device and thus it can help body around him to diagnose acute ischemia if needed, considering that the baseline is a universal electronic signal of any human electrocardiogram. Depending on the result of the ST analysis in a few ECG signal periods, the electronic analysis unit turns on an alarm if the analysis indicates the possible presence of an Acute Myocardial Infarction.

There is great public health concern as to an early diagnosis of Acute Myocardial Infarction, given that a large proportion of patients fails to seek medical attention within the first 4 to 6 hours of the onset of chest pain. If proper medical diagnosis and care are provided within this critical period (of the initial 4 to 6 hours), many lives can be saved with the use of thrombolysis drugs or any other treatment that can be furnished upon further investigation. It is for these cases that the CARDIOST is intended.

Further objects and advantages of our invention will become apparent upon consideration of the drawings and ensuing description.

DESCRIPTION OF DRAWINGS

In the drawings, closely related figures have the same number but different alphabetic suffixes.

FIGS. 2E 2F and 2G show a shift of the ST segment above the baseline which triggers a green alarm between 0–1 millimeters or 0–100 microvolts, yellow alarm between 1–2 millimeters or 100–200 microvolts and red alarm between 2 millimeters or 200 microvolts or over.

Figure 1A:
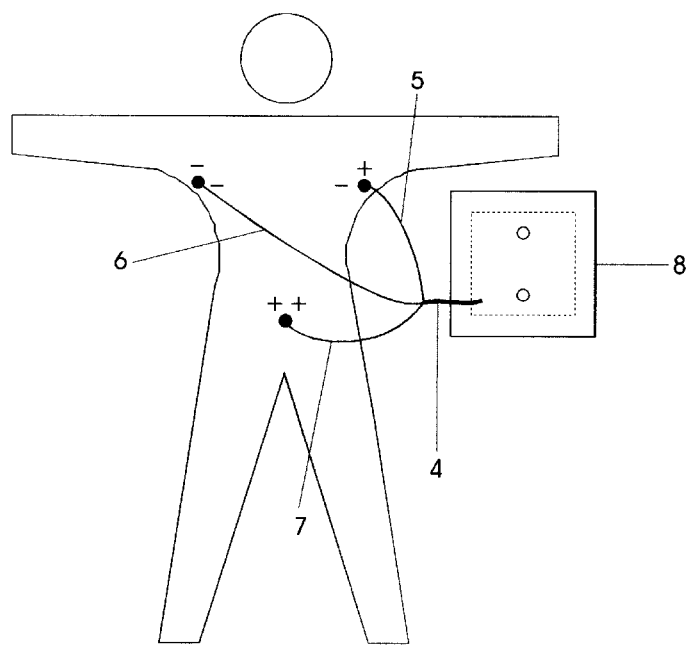
FIGS. 1A and 1B show how the CARDIOST portable electrocardiographic device is attached with a negative wire to the right armpit, with a positive/negative wire to the left armpit, and a positive wire to the lower part of the abdomen the hipogastrium. Behind the CARDIOST there is a positive and negative electrode placed in a V4 position at the $6^{th}$ to $8^{th}$ intercostal space with mid-clavicular line. These electrodes may be placed against the skin without any gel or conductive substance.

REFERENCE NUMBERS IN DRAWINGS 4 common cable
5 positive/negative left armpit cable
6 negative right armpit cable
7 positive abdomen cable
8 cardiost
9 ST segment
10 baseline
11 V4 positive electrode
12 neutral electrode
13 battery compartment
14 J point
15 ECG amplifier
16 analog to Digital Converter
17 microcontroller Unit
18 green alarm light
19 yellow alarm light
20 red alarm light
21 audible tone alarm
22 T wave

DETAILED DESCRIPTION OF THE INVENTION

Figure 1B:
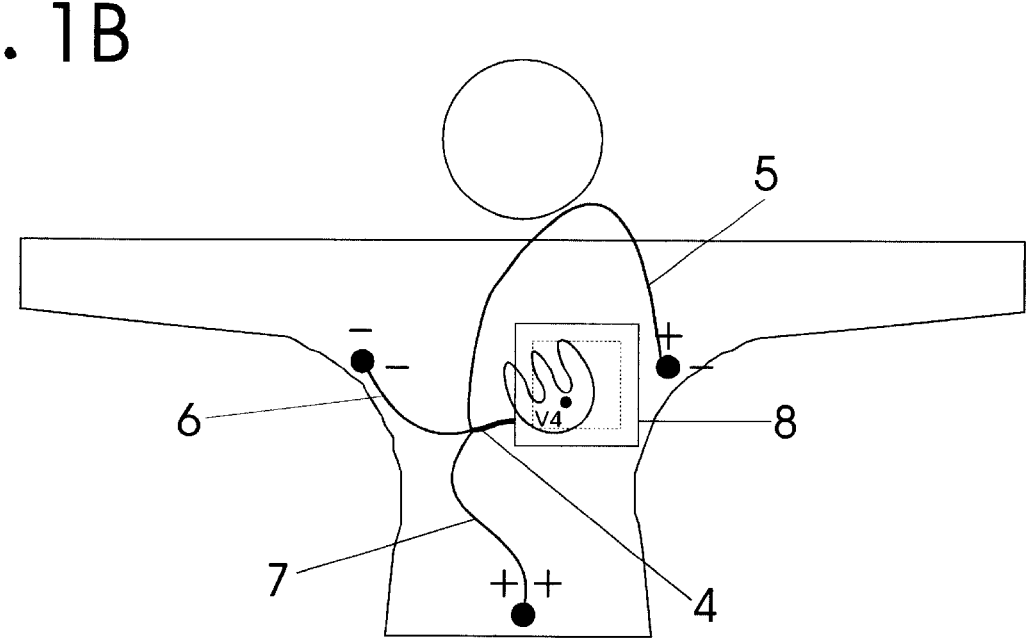

As illustrated in FIG. 1A (top view) and FIG. 1B (end view) a device 8 is comprised of a plastic housing which has a permanently attached electrode cable extending from it, 4, a cable has 3 electrode lead inputs located at the remote end, 5,6,7 and these leads connect to electrodes placed in contact with the patient's body to provide electrical input of his/her electrocardiographic signals. In the right armpit the electrode is negative 6, in the left armpit the electrode is positive/negative 5, and in the lower portion of the abdomen, the hipogastrium, the electrode is positive 7.

Figure 1C:
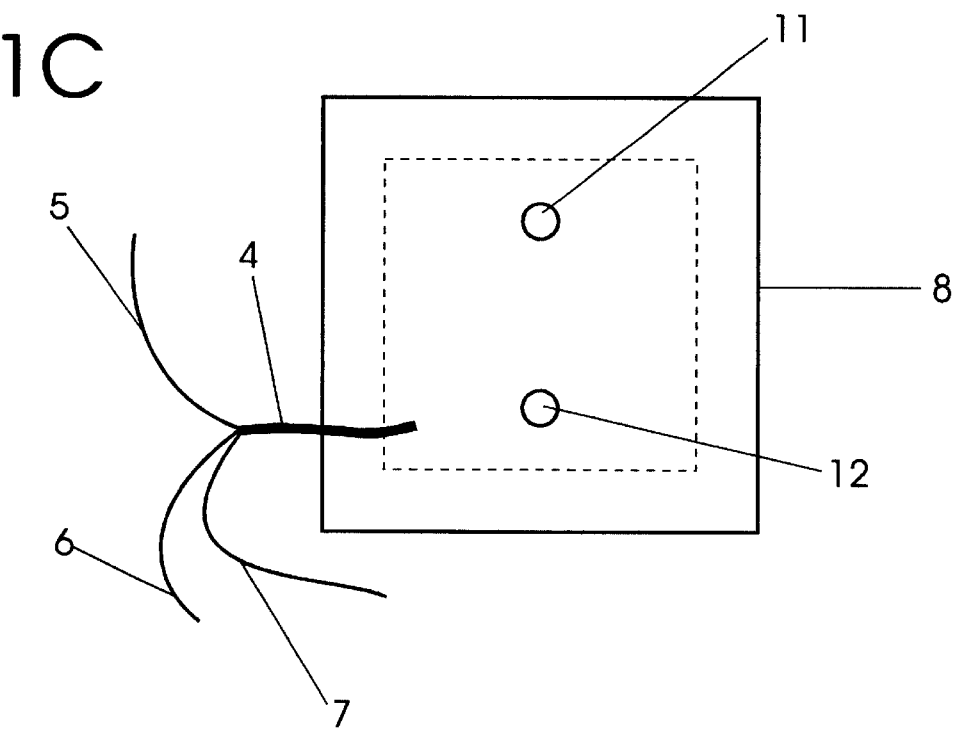
FIG. 1C shows a CARDIOST device from the rear with the neural electrode and precordial positive electrode that are intended to be placed in the precordial area V4.

As illustrated in FIG. 1C, at the rear end of a device 8 a positive electrode 11 is used to be placed in the precordial area in V4 to record one electrocardiographic signal that we think is enough for diagnosis of the anterior wall of the heart. A neutral electrode 12 is also shown.

Figure 1D:
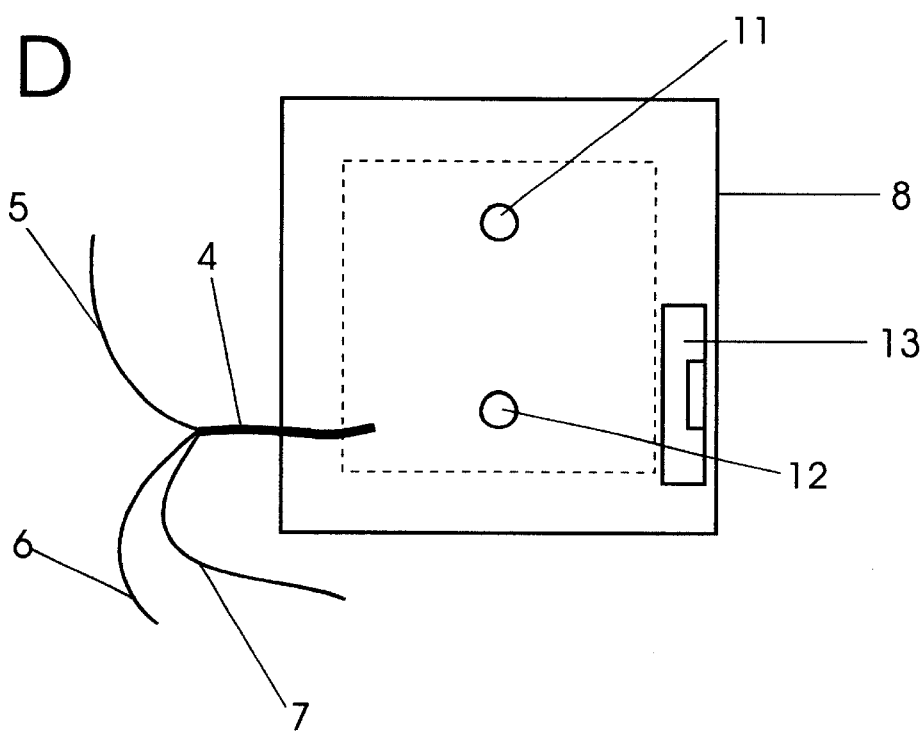
FIG. 1D shows the rear of the device and the battery compartment.

As illustrate in FIG. 1D, a battery compartment 13 is located within a device 8, preferably for 1.5 volt alkaline (size AA/AAA) disposable batteries to supply power. A device 8 may be placed in a carrying case, to be used by the patient at any time at night or day, when feeling a chest pain. Since a device may be used immediately at any time, the patient will have a high probability of ensuring a timely diagnosis.

Figure 2A:
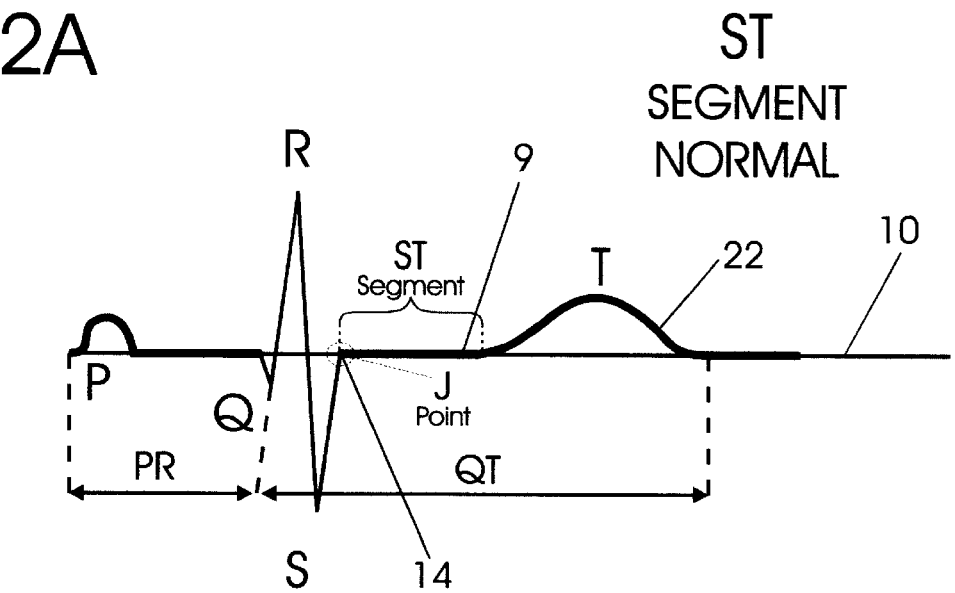
FIG. 2A shows a normal electrocardiogram with the baseline and normal waves named P, QRS, T and electrocardiographic segments PR, ST and QT. The J point is determined as the point where the QRS reaches the baseline.

As illustrated in FIG. 2A, a normal electrocardiogram has P as the first positive wave of the electrocardiogram for auricular contraction, Q as the first negative wave of the electrocardiogram, R as the second positive wave, and S as the second negative wave, which make up the QRS complex for ventricular contraction, the ST segment 9 from the J point 14 to the beginning of T wave 22, 80 miliseconds past this J point 14, where ischemia factors are detected, and T wave 22 the last positive wave of the electrocardiogram which accounts for ventricular repolarization. A baseline 10 is the basic line between P, QRS and T wave 22.

Figure 2B:
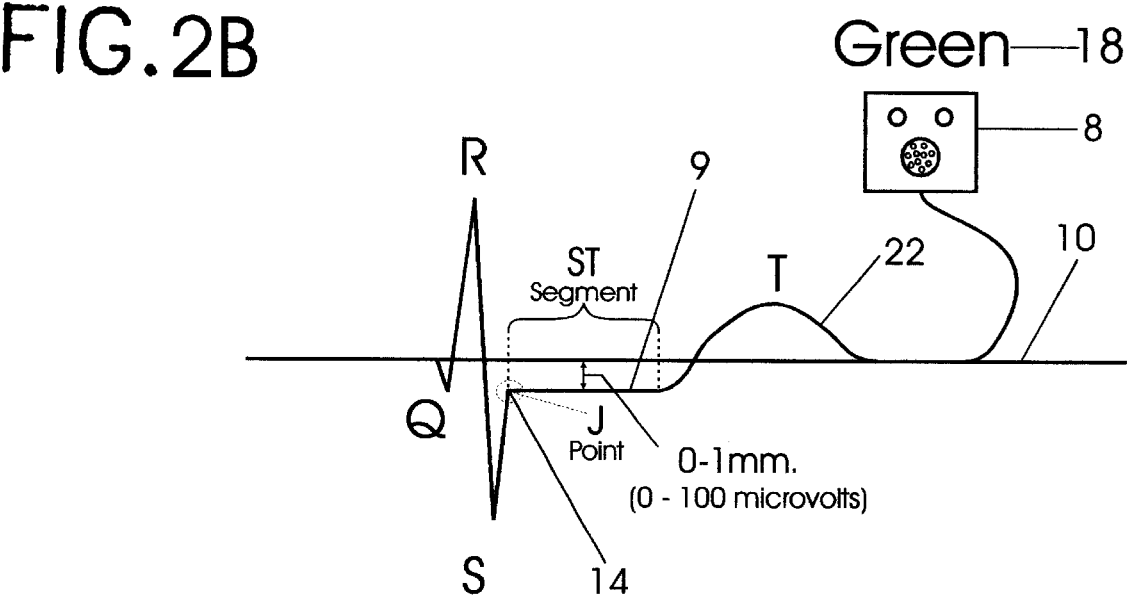
FIGS. 2B 2C and 2D show a shift of ST segment below the baseline which triggers a green alarm between 0–1 millimeters or 0–100 microvolts, yellow alarm between 1–2 millimeters or 100–200 microvolts and red alarm between 2 millimeters or 200 microvolts or over.
Figure 2C:
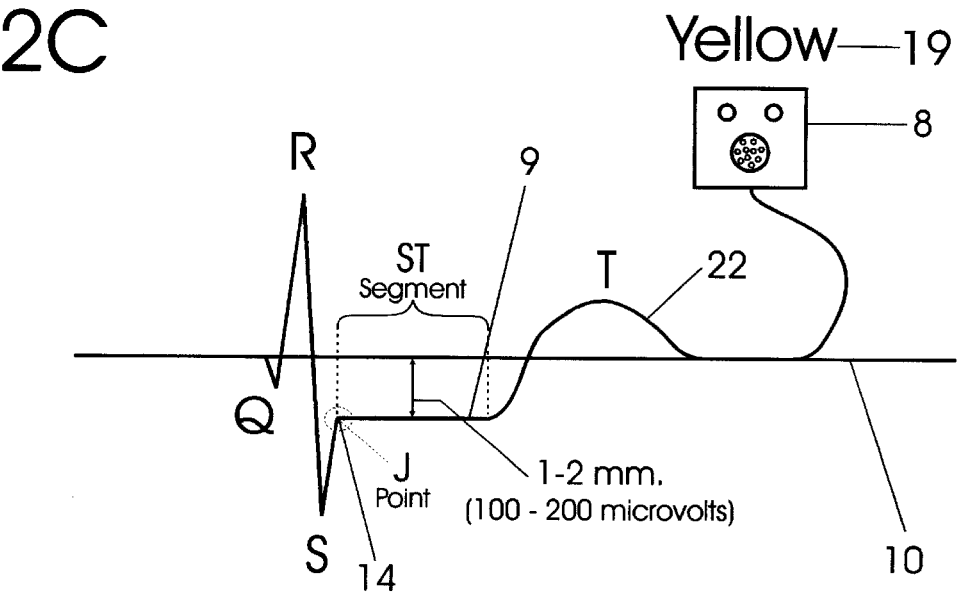
Figure 2D:
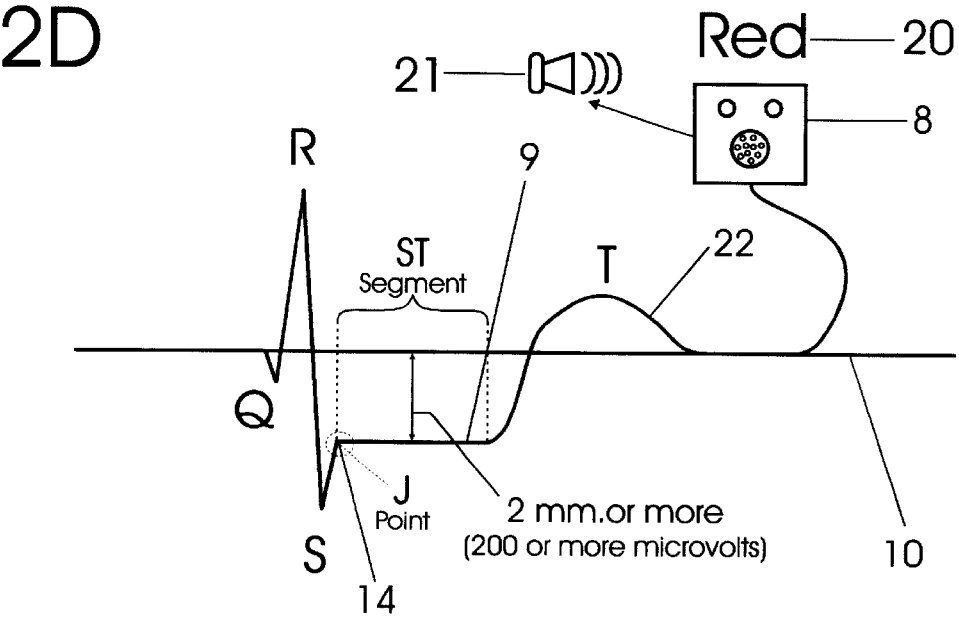

As illustrated in FIG. 2B, this shift of the ST segment 9 can range negative from 0 to 1 millimeters (0 to 100 microvolts) to be considered as low risk (green light 18), in FIG. 2C segment ST 9 from 1 to 2 millimeters negative (100 to 200 microvolts) to be considered as medium risk yellow light 19) and in FIG. 2D segment ST 9 from 2 millimeters and over negative (200 microvolts or over) to be considered as high risk (red light 20) for Acute Myocardial Infarction of the subendocardial type.

Figure 2E:
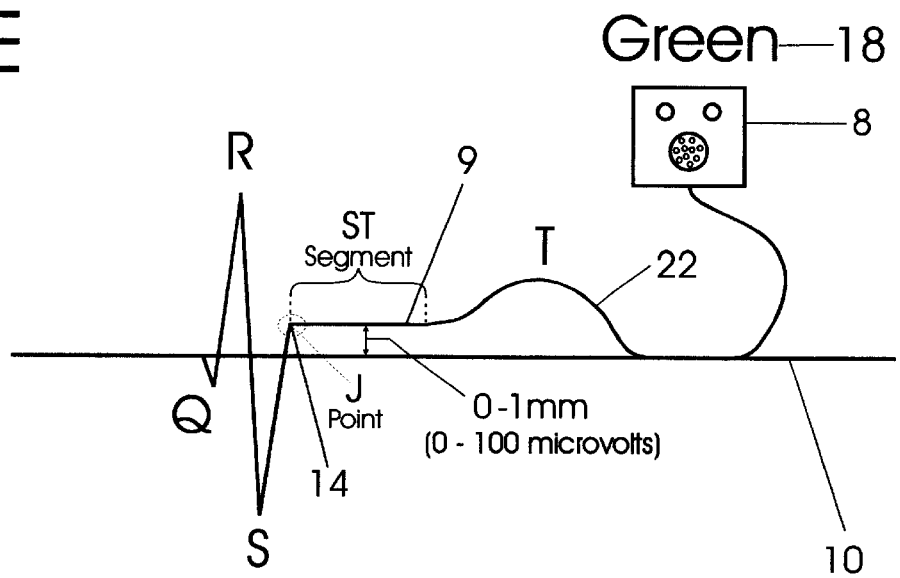
Figure 2F:
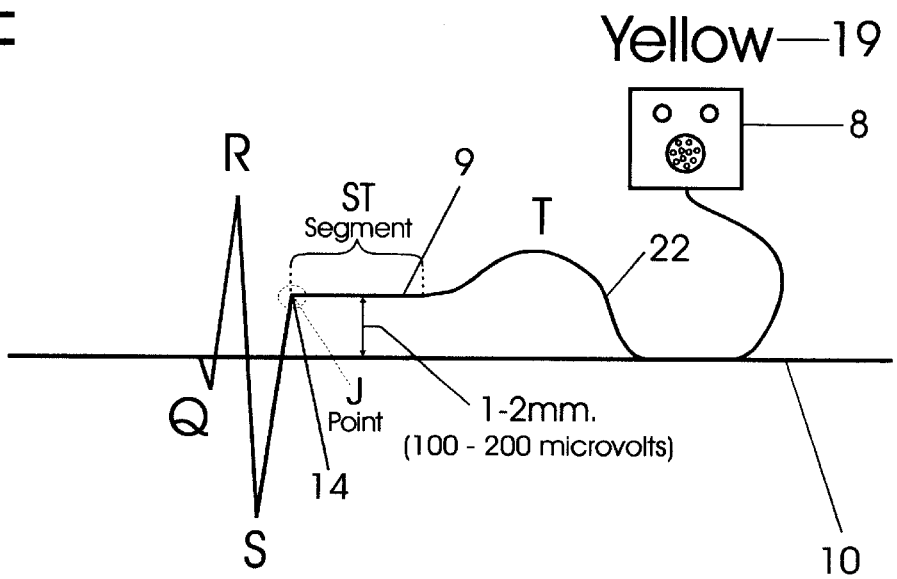

As illustrated in FIG. 2E this shift of the ST segment 9 can range positive from 0 to 1 millimeters (0 to 100 microvolts) to be considered as low risk (green light 18), in FIG. 2F segment ST 9 from 1 to 2 millimeters positive (100 to 200 microvolts) to be considered as medium risk (yellow light 19) and in FIG. 2G segment ST 9 from 2 millimeters and over positive (200 microvolts or over) to be considered as high risk (red light 20) for Acute Myocardial Infarction of the subepicardial type.

Figure 3A:
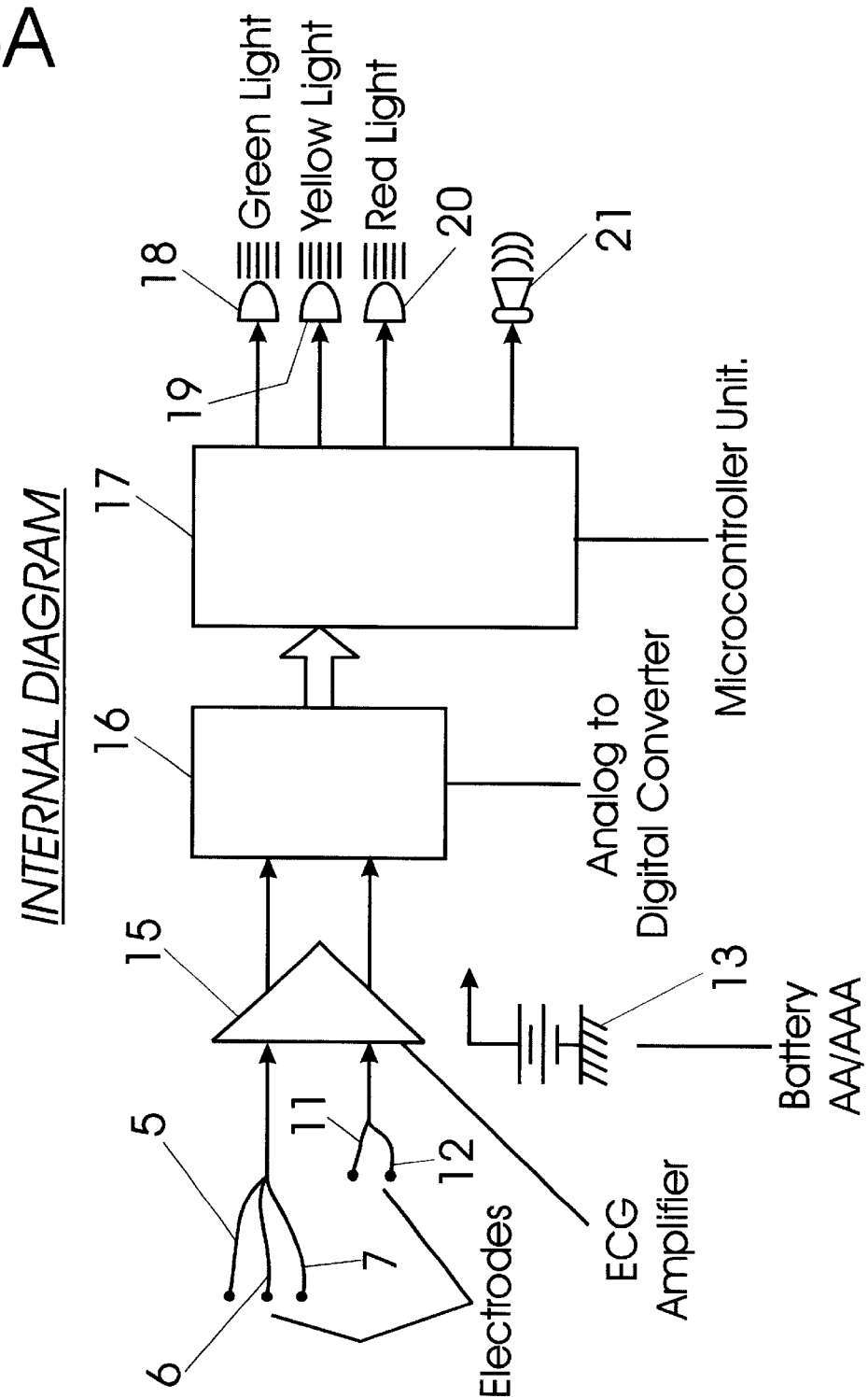
FIG. 3A shows an internal diagram of the device with the electrodes entering an instrumentation amplifier that sends signals to the Analog to Digital Converter (ADC) reading the ECG in real time and triggering the respective alarm.

As illustrated in FIG. 3A a device consists of electrodes 5,6,7 and positive and neutral electrodes 11 and 12 entering an instrumentation electrocardiographic amplifier 15 which sends the signals in a voltage range suitable for a Analog to Digital Converter (ADC) 16. By means of the ADC, a microcontroller 17 reads the electrocardiographic data in real time and after processing the information triggers the appropriate alarm green 18 for low risk of Acute Myocardial Infarction (AMI), yellow 19 for medium risk AMI or red 20 and audible tone 21 for high risk of AMI. Batteries 13 are also shown.

Figure 3B:
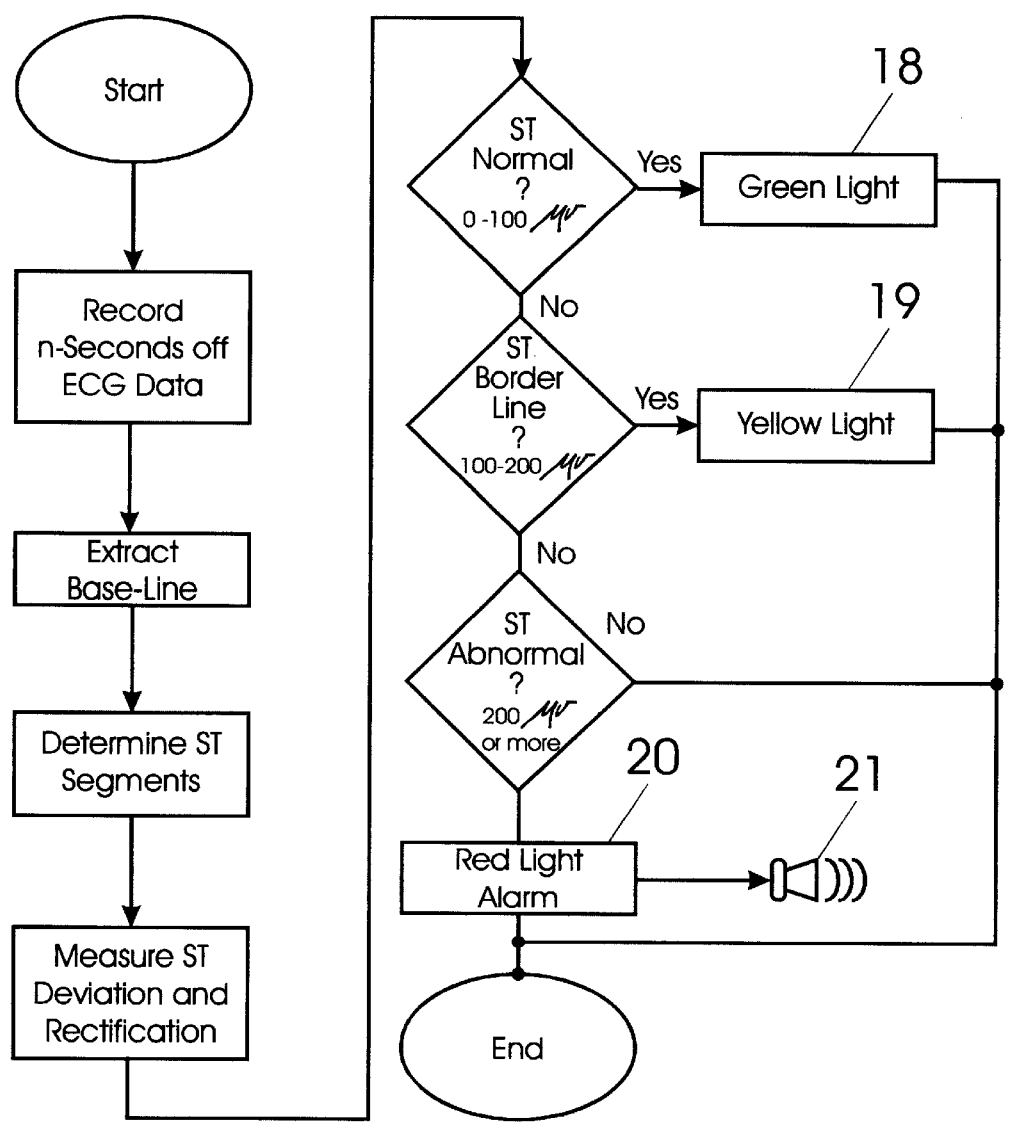
FIG. 3B show the program flow diagram used inside the microcontoller. The program measures the electrocardiographic data, extracts the baseline, determine the ST segment deviation and, depending on same, turns on the alarm where the analysis indicates the possible presence of Acute Myocardial Infarction.

As illustrated in FIG. 3B, a flow diagram used in the program is contained in a microcontroller unit. The program starts by measuring electrocardiographic data for a short time, 30 seconds, then a unit extracts the ST segment of the electrocardiographic signal and measures its elevation or depression in relation to a baseline. Depending on the result of a ST segment analysis, a electronic analysis unit turns on an alarm if the analysis indicates a possible presence of an Acute Myocardial Infarction. As shown in this FIGURE, an ST segment deviation above or below the 2 millimeters or 200 microvolts range from the baseline activates the red alarm 20 and audible alarm 21, a deviation of the ST segment between 1 and 2 millimeters or 100 to 200 microvolts above or below the baseline activates the yellow alarm 19 and no deviation or below or above the baseline 1 millimeter or 100 microvolts of the ST segment activates the green alarm 18.

Operation

With the combination of the five electrodes in the device, four active and one neutral we are able to obtain the standard electrocardiogram derivations for diagnosing Acute Myocardial Infarction in the different area of the myocardial muscle, i.e.:

(a) Inferior Myocardial Infarction with the electrode combination of DII (right armpit 6 and hipogastrium or positive abdomen cable 7), D III (left armpit 5 and hipogastrium or positive abdomen cable 7) and AVF (left armpit 5 and hipogastrium or positive abdomen cable 7)

(b) Lateral Myocardial Infarction with the electrode combination of AVL (left armpit 5 and hipogastrium or positive abdomen cable 7) and D I (right armpit 6 and left armpit 5)

(c) Anterior Myocardial Infarction with only one electrocardiographic signal obtained from the precordial lead in V4, 11 (intersection of imaginary line of seven to eight intercostal spaces with mid clavicular line).

(d) Posterior myocardial infarction with the mirror image of anterior leads (precordial electrode 11).

An electronic circuit is placed in the housing and is used by the patient by means of acoustic and light signals to assist in the diagnosis of Acute Myocardial Infarction. A green light means low risk, a yellow light means medium risk, and a red light and an audible alarm means high risk of Acute Myocardial Infarction. Thus, when the patient is under medium or high risk, as alerted by the device, he/she can seek medical help immediately in order to be administered thrombolisys or any other medical treatment (since we believe that the treatment of Acute Myocardial Infarction should improve dramatically after our CARDIOST becomes available) as fast as possible after the diagnosis. This should be done in the initial 4 to 6 hours of the myocardial infarction onset, when this treatment is currently being used with an excellent statistically proved outcome in revascularization of the affected infarct zone of the heart. After 6 hours of chest pain the thrombus is well established and thrombolisys is used with a lesser probability of success. As said above, with an improved diagnosis of myocardial ischemia, an early diagnosis, the most important factor of ischemia, will be conducive to the development of more specialized treatments so that trombolisys will be merely a part of the initial treatment of ischemia, and soon we will have other therapeutic alternatives, possibly influenced by CARDIOST. It is well known that a very large proportion of patients do not seek medical help in the initial hours of Acute Myocardial Infarction, with a subsequent increase in morbidity and mortality, simply because they are not sure about the nature of their chest pain.

We believe that CARDIOST will save many lives in the future, considering that the lack of an early diagnosis of Acute Myocardial Infarction is the leading cause in morbidity and mortality in humans and remains undertreated due to the current lack of procedures for patients to make the right interpretation of their symptoms when pain arises in settings other than a hospital or a doctors office, which is the case with 99% of the occurrences of Acute Myocardial Infarction. The device is able to diagnose Acute Myocardial Infarction in any of the different areas of the heart which may be in danger, i.e. inferior, lateral, anterior, and posterior, and any combination thereof.

CONCLUSIONS, RAMIFICATIONS, AND SCOPE OF THE INVENTION

Thus the reader will see that diagnosis of Acute Myocardial Infarction may be made by the patient himself when chest pain arises, by connecting the device to his body, thus triggering either acoustic or visual alarms. This will enable him to seek medical help 4–6 hours after symptoms arise, with the advantages of an early thrombolisys or any other treatment available, which will be made possible thanks to an early diagnosis, one of the most difficult problems to be resolved in order to minimize the high morbidity and mortality at present caused by Acute Myocardial Infarction.

Although the above description contains many specificity's, these should not be construed as limiting the scope of the CARDIOST but rather as an exemplification of a preferred embodiment thereof. Many other variations are possible. For example, the device may have other types of alarms, other cable connections, may allow for the analysis of different parts of the electrocardiogram with other diagnosis periods, other treatments proposed, analysis of other waves of the electrocardiogram, etc.

Thus the scope of the CARDIOST should be determined by the appended claims and their legal equivalents, rather than by the examples given.

We claim:

1. A method for self-diagnosis of acute myocardial infarction at the moment of chest pain indicating ischemic activity for an early diagnosis, in the first four to six hours of said acute myocardial infarction to determine with a high degree of effectiveness when an artery of the heart is acutely obstructed by trombus or rupture of atherosclerotic plaque related to said ischemic activity by means of a device attached with a negative wire to the patient's right armpit, a positive/negative wire attached to the patient's left armpit and a positive wire attached to the lower part of the patient's abdomen including the hipogastrium, and further including positive and negative electrodes placed in a V4 position at the 6th to 8th intercostal space along the midclavicular line, where the said electrodes may be placed against the skin of the patient without any gel or conductive substance, wherein said device further includes an analog to digital converter and a microcontroller, the method comprising;
   a) sensing a shift of st segment below or above a baseline, wherein a green light alarm is generated by said device if said shift is between 0–1 millimeters, or 0–100 microvolts, in absolute value and a yellow light alarm is generated by said device if said shift is between 1–2 millimeters, or 100–200 microvolts, in absolute value and a red light alarm is generated by said device if said shift is greater than 2 millimeters, or greater than 200 microvolts, in absolute value wherein said green alarm indicates low risk, said yellow alarm indicates medium risk, and said red alarm indicates high risk for said acute myocardial infarction of the subendocardial type;
   b) wherein said analog to digital converter digitizes the patient's ECG signal and inputs said digitized ECG signal into said microcontroller in real time, wherein said microcontroller processes said signal and senses said shift of st segment and further triggers said alarms.

2. A method for diagnosis of acute myocardial infarction by a device capable of sensing a patient's ECG waveform and emitting an audible and visual alarm comprising;
   a) measuring a positive or negative st segment baseline shift of a patient's ECG waveform starting at a j point which indicates part of said ECG waveform,
   b) detecting either said positive or said negative shift and sensing said j point as the point where the st segment begins, said j point being measured in real time, wherein said device emits audible and green alarms if said j point of said st segment is between 0–1 millimeters, or 100 microvolts, in absolute value, to indicate subepicardial or subendocardial ischemia where there is a low risk of acute myocardial infarction, and wherein said device emits audible and yellow alarms if said j point of said st segment is between 1–2 millimeters or 100–200 microvolts, in absolute value, to indicate subepicardial or subendocardial ischemia where there is a medium risk for acute myocardial infarction, and wherein said device emits audible and red alarms if said j point of said st segment is 2 millimeters or over, or over 200 microvolts, in absolute value, to indicate subepicardial or subendocardial ischemia where there is a high risk for acute myocardial infarction.

* * * * *